(12) United States Patent
Green et al.

(10) Patent No.: US 6,900,223 B2
(45) Date of Patent: *May 31, 2005

(54) DIHYDRODIPYRAZOLOPYRIDINONE INHIBITORS OF B7-1

(75) Inventors: Neal Jeffrey Green, Newton, MA (US); Steve Yikkai Tam, Wellesley, MA (US); Jason Shaoyun Xiang, Winchester, MA (US); Audrey Molina Davies, Arlington, MA (US); Lihren Chen, Cambridge, MA (US); Gary Paul Stack, Ambler, PA (US)

(73) Assignee: Wyeth, Madison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/629,227

(22) Filed: Jul. 28, 2003

(65) Prior Publication Data

US 2004/0044024 A1 Mar. 4, 2004

Related U.S. Application Data

(60) Provisional application No. 60/399,161, filed on Jul. 29, 2002.

(51) Int. Cl.[7] .................... A61K 31/437; C07D 471/14; A61P 37/00
(52) U.S. Cl. ................... 514/293; 514/292; 514/275; 514/258; 514/252.04; 546/82; 544/238; 544/331; 544/333
(58) Field of Search .......................... 546/82; 544/238, 544/331, 333; 514/293, 292, 275, 256, 252.04

(56) References Cited

U.S. PATENT DOCUMENTS

| 3,669,950 | A | | 6/1972 | Hoehn et al. |
| 3,787,430 | A | * | 1/1974 | Hoehn .......................... 546/12 |
| 4,560,689 | A | | 12/1985 | Yokoyama |
| 4,814,450 | A | | 3/1989 | Yokoyama |
| 6,121,257 | A | * | 9/2000 | Kawai et al. ................ 514/183 |
| 6,635,633 | B2 | * | 10/2003 | Cai et al. ................ 514/217.04 |

OTHER PUBLICATIONS

Ian T. Forbes et al., Journal of Medicinal Chemistry, 1990, vol. 33, 2640–2645.

Erbe, D. V.; Wang, S.; Xing, Y.; and Tobin, J. F.; The Journal of Biological Chemistry (2002), vol. 277, 7363–7368.

* cited by examiner

*Primary Examiner*—Evelyn Mei Huang
(74) *Attorney, Agent, or Firm*—Barbara L. Lences

(57) ABSTRACT

The present invention provides a compound of formula I and the use thereof for the immunotherapeutic treatment of transplant rejection, autoimmune disease or graft vs. host disease.

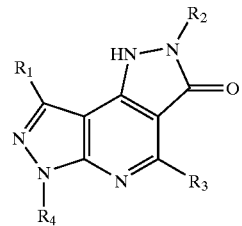

(I)

15 Claims, No Drawings

DIHYDRODIPYRAZOLOPYRIDINONE INHIBITORS OF B7-1

This application claims priority from provisional application Ser. No. 60/399,161, filed Jul. 29, 2002, the entire disclosure of which is hereby incorporated by reference.

BACKGROUND OF THE INVENTION

Regulation of T cell responses plays a primary role in determining the outcome of auto-immune disease, the development of tumor immunity, and graft survival following transplantation (Bluestone, et.al. *Annu, Rev. Immunol.* 1996, 14, 233–258.; Kuchroo, et. al. *Crit. Rev. Immunol.* 1998, 18, 389–418.; Guinan, et. al. *N. Engl. J. Med.* 1999, 340, 1704–1714.; Abrams et. al. *J. Exp. Med.* 2000, 192, 681–694). These immune responses are controlled by the interaction of molecules on T cell and antigen presenting cell surfaces. Activation of T cells requires two signals, an antigen-specific signal delivered through T cell antigen receptor, and a second co-stimulatory signal. This co-stimulatory signal dictates the outcome for T cells through the binding of B7-1 and B7-2 expressed on antigen presenting cells to CD28 and CTLA-4 on T cells. CD28 engagement by B7-1 or B7-2 amplifies T cell receptor signaling and stimulates production of cytokines required for T-cell proliferation. On the other hand, CTLA-4 engagement by B7-1 or B7-2 down regulates the immune response (Allison, et. al. *Nature* 1992, 356, 607–609.; Bluestone, et. al. *Immunity* 1994, 1, 405–413.; Thompson, et. al. *Science* 1995, 270, 985–988). In experimental disease models, altering these co-stimulatory signals has profound effects on immunity. Blocking B7/CD28 interactions with monoclonal antibodies or soluble receptors results in immunosuppression and enhanced allograft survival, while B7/CTLA-4 blockade results in enhanced anti-tumor immune responses (Larsen, et. al. *Nature* 1996, 381, 434–438). Consequently, agents, such as small molecules, which act as inhibitors of cell-cell interactions may be useful in the development of effective immunomodulatory medicines.

Therefore, it is an object of this invention to provide compounds which are useful as immunotherapeutic agents in the treatment of transplant rejection, autoimmune disease or graft vs host disease.

It is another object of this invention to provide therapeutic methods and pharmaceutical compositions useful for the treatment of transplant rejection, autoimmune disease or graft vs host disease.

It is a feature of this invention that the compounds provided may be used to further study and elucidate the interactions of B7-1 with the CD28 receptor.

These and other objects and features of the invention will become more apparent by the detailed description set forth hereinbelow.

SUMMARY OF THE INVENTION

The present invention provides a compound of formula I

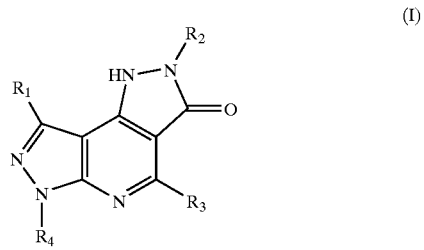

(I)

wherein $R_1$ and $R_4$ are each independently H, $C_1$–$C_{10}$alkyl optionally substituted with one or more halogen, hydroxy, $C_1$–$C_4$alkoxy, $CO_2R_6$, $CONR_7R_8$, $C_3$–$C_7$cycloalkyl or optionally substituted phenyl groups, or
  phenyl optionally substituted with one to three halogen, hydroxy, $C_1$–$C_6$haloalkyl, $C_1$–$C_4$alkoxy, $CO_2R_9$, $NR_{10}R_{11}$ or CN groups;

$R_2$ is H, $C_1$–$C_6$alkyl optionally substituted with a phenyl, naphthyl or heteroaryl group each group optionally substituted with one to three $C_1$–$C_6$alkyl, $C_1$–$C_6$haloalkyl, $C_1$–$C_4$alkoxy, hydroxy, CHO, $NO_2$, CN, $CO_2R_{12}$ or $NR_{13}R_{14}$ groups,
  phenyl optionally substituted with one to three halogen, $NO_2$, CN, hydroxy, $C_1$–$C_6$alkyl, $C_1$–$C_6$haloalkyl, $C_1$–$C_6$alkoxy, phenyl, phenoxy, benzyl, benzyloxy, $CO_2R_{17}$, $NR_{18}R_{19}$ or $CH_2CO_2R_{20}$ groups,
  naphthyl optionally substituted with one to three halogen, $NO_2$, CN, hydroxy, $C_1$–$C_6$alkyl, $C_1$–$C_6$haloalkyl, $C_1$–$C_6$alkoxy, phenyl, phenoxy, benzyl, benzyloxy, $CO_2R_{17}$, $NR_{18}R_{19}$ or $CH_2CO_2R_{20}$ groups,
  $C_5$–$C_7$cycloheteroalkyl optionally substituted with one to three halogen, $NO_2$, CN, $C_1$–$C_6$alkyl, $C_1$–$C_6$haloalkyl, $C_1$–$C_4$alkoxy, $CO_2R_{17}$ or $NR_{18}R_{19}$ groups, or
  heteroaryl optionally substituted with one to three halogen, $NO_2$, CN, $C_1$–$C_6$alkyl, $C_1$–$C_6$haloalkyl, $C_1$–$C_4$alkoxy, $CO_2R_{17}$ or $NR_{18}R_{19}$ groups;

$R_3$ is phenyl optionally substituted with one to three halogen, $NO_2$, CN, hydroxy, $C_1$–$C_6$alkyl, $C_1$–$C_6$alkylthio, $C_1$–$C_6$haloalkyl, $C_1$–$C_6$alkoxy, phenyl, phenoxy, benzyl, benzyloxy, $SO_nR_{26}$, $SO_2NR_{21}R_{22}$, $CO_2R_{23}$ or $NR_{24}R_{25}$ groups,
  cycloheteroalkyl optionally substituted with one or more halogen, $NO_2$, CN, hydroxy, $C_1$–$C_6$alkyl, $C_1$–$C_6$alkylthio, $C_1$–$C_6$haloalkyl, $C_1$–$C_6$alkoxy, phenyl, phenoxy, benzyl, benzyloxy, $SO_nR_{26}$, $SO_2NR_{21}R_{22}$, $CO_2R_{23}$ or $NR_{24}R_{25}$ groups, or
  heteroaryl optionally substituted with one or more halogen, $NO_2$, CN, hydroxy, $C_1$–$C_6$alkyl, $C_1$–$C_6$alkylthio, $C_1$–$C_6$haloalkyl, $C_1$–$C_6$alkoxy, phenyl, phenoxy, benzyl, benzyloxy, $SO_nR_{26}$, $SO_2NR_{21}R_{22}$, $CO_2R_{23}$ or $NR_{24}R_{25}$ groups;

$R_6$, $R_9$, $R_{12}$, $R_{17}$, $R_{20}$ and $R_{26}$ are each independently H or a $C_1$–$C_6$alkyl, $C_3$–$C_7$ cycloalkyl, $C_1$–$C_6$haloalkyl, phenyl, $C_5$–$C_7$cycloheteroalkyl or heteroaryl group each optionally substituted;

n is 0 or an integer of 1 or 2; and $R_7$, $R_8$, $R_{10}$, $R_{11}$, $R_{13}$, $R_{14}$, $R_{18}$, $R_{19}$, $R_{21}$, $R_{22}$, $R_{24}$ and $R_{25}$ are each independently H or a $C_1$–$C_6$alkyl, $C_3$–$C_7$cycloalkyl, $C_1$–$C_6$haloalkyl, phenyl, $C_5$–$C_7$cycloheteroalkyl or heteroaryl group each optionally substituted or each of $R_7$ and $R_8$ or $R_{10}$ and $R_{11}$ or $R_{13}$ and $R_{14}$ or $R_{18}$ and $R_{19}$ or $R_{21}$ and $R_{22}$ or $R_{24}$ and $R_{25}$ may be taken together with the nitrogen atom to which they are attached to form a 5- to 7-membered ring optionally containing another heteroatom selected from O, N or S; or the stereoisomers thereof or the pharmaceutically acceptable salts thereof.

The present invention also provides methods and compositions useful for the immunotherapeutic treatment of transplant rejection, autoimmune disease or graft vs host disease.

DETAILED DESCRIPTION OF THE INVENTION

Full T cell activation requires both an antigen-specific and a second co-stimulatory signal. Co-stimulation dictates the outcome for T cells through the binding of B7-1 and B7-2 expressed on antigen-presenting cells to CD28 and CTLA4 on T cells (Greenfield, E. A., Nguyen, K. A. and Kuchroo, V. K. (1998) Critical Review of Immunology, 18, 389–418 and Lenschow, D. J., Walunas, T. L. and Bluestone, J. A. (1996) Annual Review of Immunology, 14, 233–258). Animal studies and clinical trials with protein antagonists of these interactions indicate considerable promise for immunotherapy in transplantation and autoimmune disease.

Surprisingly, it has now been found that dihydrodipyrazolopyridinone compounds of formula I are effective inhibitors of B7-1/CD28 binding. Equilibrium dialysis demonstrates that compounds of formula I bind specifically to human B7-1 at a common site. Occupancy of this site by said inhibitors blocked B7-1 binding not only to CD28, but also to CTLA-4 (although at much higher concentrations of inhibitor). Accordingly, the present invention provides dihydrodipyrazolopyridinone B7-1 inhibitors of formula I

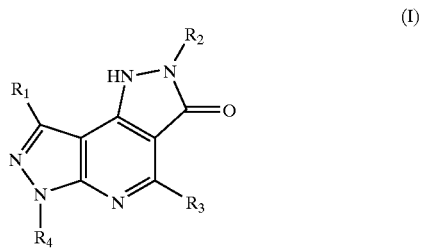

(I)

wherein $R_1$ and $R_4$ are each independently H, $C_1$–$C_{10}$alkyl optionally substituted with one or more halogen, hydroxy, $C_1$–$C_4$alkoxy, $CO_2R_6$, $CONR_7R_8$, $C_3$–$C_7$cycloalkyl or optionally substituted phenyl groups, or phenyl optionally substituted with one to three halogen, hydroxy, $C_1$–$C_6$haloalkyl, $C_1$–$C_4$alkoxy, $CO_2R_9$, $NR_{10}R_{11}$ or CN groups;

$R_2$ is H, $C_1$–$C_6$alkyl optionally substituted with a phenyl, naphthyl or heteroaryl group each group optionally substituted with one to three $C_1$–$C_6$alkyl, $C_1$–$C_6$haloalkyl, $C_1$–$C_4$alkoxy, hydroxy, CHO, $NO_2$, CN, $CO_2R_{12}$ or $NR_{13}R_{14}$ groups, phenyl optionally substituted with one to three halogen, $NO_2$, CN, hydroxy, $C_1$–$C_6$alkyl, $C_1$–$C_6$haloalkyl, $C_1$–$C_6$alkoxy, phenyl, phenoxy, benzyl, benzyloxy, $CO_2R_{17}$, $NR_{18}R_{19}$ or $CH_2CO_2R_{20}$ groups, naphthyl optionally substituted with one to three halogen, $NO_2$, CN, hydroxy, $C_1$–$C_6$alkyl, $C_1$–$C_6$haloalkyl, $C_1$–$C_6$alkoxy, phenyl, phenoxy, benzyl, benzyloxy, $CO_2R_{17}$, $NR_{18}R_{19}$ or $CH_2CO_2R_{20}$ groups, $C_5$–$C_7$cycloheteroalkyl optionally substituted with one to three halogen, $NO_2$, CN, $C_1$–$C_6$alkyl, $C_1$–$C_6$haloalkyl, $C_1$–$C_4$alkoxy, $CO_2R_{17}$ or $NR_{18}R_{19}$ groups, or heteroaryl optionally substituted with one to three halogen, $NO_2$, CN, $C_1$–$C_6$alkyl, $C_1$–$C_6$haloalkyl, $C_1$–$C_4$alkoxy, $CO_2R_{17}$ or $NR_{18}R_{19}$ groups;

$R_3$ is phenyl optionally substituted with one to three halogen, $NO_2$, CN, hydroxy, $C_1$–$C_6$alkyl, $C_1$–$C_6$alkylthio, $C_1$–$C_6$haloalkyl, $C_1$–$C_6$alkoxy, phenyl, phenoxy, benzyl, benzyloxy, $SO_nR_{26}$, $SO_2NR_{21}R_{22}$, $CO_2R_{23}$ or $NR_{24}R_{25}$ groups, cycloheteroalkyl optionally substituted with one or more halogen, $NO_2$, CN, hydroxy, $C_1$–$C_6$alkyl, $C_1$–$C_6$alkylthio, $C_1$–$C_6$haloalkyl, $C_1$–$C_6$alkoxy, phenyl, phenoxy, benzyl, benzyloxy, $SO_nR_{26}$, $SO_2NR_{21}R_{22}$, $CO_2R_{23}$ or $NR_{24}R_{25}$ groups, or heteroaryl optionally substituted with one or more halogen, $NO_2$, CN, hydroxy, $C_1$–$C_6$alkyl, $C_1$–$C_6$alkylthio, $C_1$–$C_6$haloalkyl, $C_1$–$C_6$alkoxy, phenyl, phenoxy, benzyl, benzyloxy, $SO_nR_{26}$, $SO_2NR_{21}R_{22}$, $CO_2R_{23}$ or $NR_{24}R_{25}$ groups;

$R_6$, $R_9$, $R_{12}$, $R_{17}$, $R_{20}$ and $R_{26}$ are each independently H or a $C_1$–$C_6$alkyl, $C_3$–$C_7$ cycloalkyl, $C_1$–$C_6$haloalkyl, phenyl, $C_5$–$C_7$cycloheteroalkyl or heteroaryl group each optionally substituted;

n is 0 or an integer of 1 or 2; and $R_7$, $R_8$, $R_{10}$, $R_{11}$, $R_{13}$, $R_{14}$, $R_{18}$, $R_{19}$, $R_{21}$, $R_{22}$, $R_{24}$ and $R_{25}$ are each independently H or a $C_1$–$C_6$alkyl, $C_3$–$C_7$cycloalkyl, $C_1$–$C_6$haloalkyl, phenyl, $C_5$–$C_7$cycloheteroalkyl or heteroaryl group each optionally substituted or each of $R_7$ and $R_8$ or $R_{10}$ and $R_{11}$ or $R_{13}$ and $R_{14}$ or $R_{18}$ and $R_{19}$ or $R_2$, and $R_{22}$ or $R_{24}$ and $R_{25}$ may be taken together with the nitrogen atom to which they are attached to form a 5- to 7-membered ring optionally containing another heteroatom selected from O, N or S; or the stereoisomers thereof or the pharmaceutically acceptable salts thereof.

As used in the specification and claims, the term halogen designates F, Cl, Br or I and the term cycloheteroalkyl designates a $C_5$–$C_7$cycloalkyl ring system containing 1 or 2 heteroatoms, which may be the same or different, selected from N, O or S and optionally containing one double bond. Exemplary of the cycloheteroalkyl ring systems included in the term as designated herein are the following rings wherein X is NR, O or S; and R is H or an optional substituent as described hereinbelow:

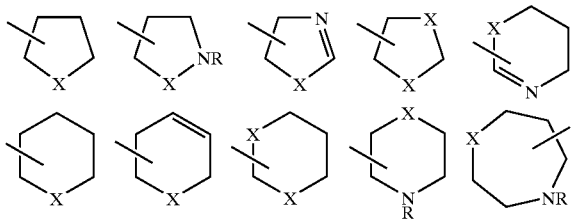

Similarly, as used in the specification and claims, the term heteroaryl designates a $C_5$–$C_{10}$ aromatic ring system containing 1, 2 or 3 heteroatoms, which may be the same or different, selected from N, O or S. Such heteroaryl ring systems include pyrrolyl, azolyl, oxazolyl, thiazolyl, imidazolyl, furyl, thienyl, quinolinyl, isoquinolinyl, indolinyl, benzothienyl, benzofuranyl, benzisoxazolyl or the like. The term aryl designates a carbocyclic aromatic ring system such as phenyl, naphthyl, anthracenyl or the like. The term haloalkyl as used herein designates a $C_nH_{2n+1}$ group having from one to 2n+1 halogen atoms which may be the same or different and the term haloalkoxy as used herein designates an $OC_nH_{2n+1}$ group having from one to 2n+1 halogen atoms which may be the same or different.

In the specification and claims, when the terms $C_1$–$C_6$alkyl, $C_2$–$C_6$alkenyl, $C_2$–$C_6$alkynyl, $C_3$–$C_7$cycloalkyl, cycloheteroalkyl, aryl or heteroaryl are designated as being optionally substituted, the substituent groups which are optionally present may be one or more of those customarily employed in the development of pharmaceutical compounds or the modification of such compounds to influence their structure/activity, persistence, absorption, stability or other beneficial property. Specific examples of such substituents include halogen atoms, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsulphinyl, alkylsulphonyl, carbamoyl, alkylamido, phenyl, phenoxy, benzyl, benzyloxy, heterocyclyl or cycloalkyl groups, preferably halogen atoms, $NO_2$ or $CF_3$ groups. Typically, 0–3 substituents may be present, preferably 1 or 2. When any of the foregoing substituents represents or contains an alkyl substituent group, this may be linear or branched and may contain up to 12, preferably up to 6, more preferably up to 4 carbon atoms.

Pharmaceutically acceptable salts may be any acid addition salt formed by a compound of formula I and a pharmaceutically acceptable acid such as phosphoric, sulfuric, nitric, hydrochloric, hydrobromic, citric, malic, maleic, malonic, mandelic, succinic, fumaric, tartaric, propionic, acetic, lactic, nitric, sulfonic, p-toluene sulfonic, methane sulfonic acid or the like.

Compounds of the invention include esters, carbamates or other conventional prodrug forms, which in general, are functional derivatives of the compounds of the invention and which are readily converted to the inventive active moiety in vivo. Correspondingly, the method of the invention embraces the treatment of the various conditions described hereinabove with a compound of formula I or with a compound which is not specifically disclosed but which, upon administration, converts to a compound of formula I in vivo. Also included are metabolites of the compounds of the present invention defined as active species produced upon introduction of these compounds into a biological system.

Compounds of the invention may exist as one or more stereoisomers. The various stereoisomers include enantiomers, diastereomers, atropisomers and geometric isomers. One skilled in the art will appreciate that one stereoisomer may be more active or may exhibit beneficial effects when enriched relative to the other stereoisomer(s) or when separated from the other stereoisomer(s). Additionally, the skilled artisan knows how to separate, enrich or selectively prepare said stereoisomers. Accordingly, the present invention comprises compounds of Formula I, the stereoisomers thereof and the pharmaceutically acceptable salts thereof. The compounds of the invention may be present as a mixture of stereoisomers, individual stereoisomers, or as an optically active or enantiomerically pure form.

Preferred compounds of the invention are those compounds of the invention are those compounds of formula I wherein $R_2$ is an optionally substituted phenyl or heteroaryl group. Also preferred are those compounds of formula I wherein $R_1$ is H. Another group of preferred compounds of formula I are those compounds wherein $R_3$ is a $C_5$–$C_7$cycloheteroalkyl, heteroaryl or phenyl group each optionally substituted with one or two halogen, CN, $NO_2$, $CF_3$, methoxy, carboxy or $SOR_{26}$ groups.

More preferred compounds of the invention are those compounds of formula I wherein $R_2$ is an optionally substituted phenyl or heteroaryl group and $R_4$ is H, phenyl or $C_1$–$C_4$alkyl optionally substituted with one hydroxy or phenyl group. Another group of more preferred compounds are those compounds of formula I wherein $R_2$ is an optionally substituted phenyl or heteroaryl group and $R_3$ is a thienyl, pyridyl or phenyl group each optionally substituted with one or two halogen, CN, $NO_2$, $CF_3$, methoxy, carboxy or $SOCH_3$ groups. Further more preferred compounds of formula I are those compounds wherein $R_1$ is H; $R_2$ is a phenyl group substitued with one or two halogen; and $R_3$ is a phenyl group substituted with one $NO_2$ or $CF_3$ group.

Examples of the preferred compounds of formula I include:

2-(3-fluorophenyl)-4-(3-nitrophenyl)-1,6-dihydrodipyrazolo[3,4-b:3',4'-d]pyridin-3(2H)-one;

2-(3-fluorophenyl-6-methyl-4-(3-nitrophenyl)-1,6-dihydrodipyrazolo[3,4-b:3',4'-d]-pyridin-3(2H)-one;

2-(4-chlorophenyl)-6-methyl-4-[3-(trifluoromethyl) phenyl]-1,6-dihydrodipyrazolo-[3,4-b:3',4'-d]pyridin-3 (2H)-one;

2-(4-chlorophenyl)-6-methyl-4-(3-fluorophenyl)-1,6-dihydrodipyrazolo-[3,4-b:3'4'-d]pyridin-3(2H)-one;

4-(5-bromo-3-pyridinyl)-6-methyl-3-[(trifluoromethyl) phenyl]-1,6-dihydrodipyrazolo-[3,4-b:3',4'-d]pyridin-3 (2H)-one;

4-(5-bromo-3-pyridinyl)-3-(4-fluorophenyl)-6-methyl-1,6-dihydrodipyrazolo-[3,4-b:3',4'-d]pyridin-3-(2H)-one;

methyl 3-{6-methyl-3-oxo-4-[3-(trifluoromethyl)phenyl]-3,6-dihydrodipyrazolo-[3,4-b:3',4'-d]pyridin-2(1H)-yl}benzoate;

2-chloro-5-{6-methyl-3-oxo-4-[3-(trifluoromethyl)phenyl]-3,6-dihydrodipyrazolo-[3,4-b:3',4'-d]pyridin-2(1H)-yl}benzoic acid;

4-(3-bromophenyl)-6-methyl-2-(4-nitrophenyl)-1,6-dihydrodipyrazolo[3,4-b:3',4'-d]-pyridin-3(2H)-one;

4-[4-(3-bromophenyl)-6-methyl-3-oxo-3,6-dihdrodipyrazolo[3,4-b:3',4'-d]pyridin-2(1H)-yl-2-chlorobenzoic acid;

methyl 2-fluoro-4-{6-methyl-3-oxo-4-[3-(trifluoromethyl) phenyl]-3,6-dihydrodipyrazolo-[3,4-b:3',4'-d]pyridin-2-(1H)-yl}benzoate;

the stereoisomers thereof; or the pharmaceutically acceptable salts thereof.

Compounds of formula I may be prepared using conventional synthetic methods and, if required, standard separation or isolation techniques.

For example, for compounds of formula I wherein $R_1$ is H (Ia), an aryl, heteroaryl or heterocycloalkyl ester of formula II may undergo a Knoevenagel condensation to give the oxo ester of formula III; said oxo ester is allowed to react with an aminopyrazole of formula IV in the presence of a base to give the hydroxypyrazalopyridine of formula V; said hydroxypyrazolopyridine is then converted to the corresponding chloro compound of formula VI via reaction with a chlorinating agent such as thionyl chloride or phosphorous oxychloride; the resultant chloro compound may undergo an addition-elimination reaction with a hydrazine of formula VII to give the hydrazinyl intermediate of formula VIII; and cyclization of the formula VIII compound gives the desired product of formula Ia. The reaction is illustrated in flow diagram I.

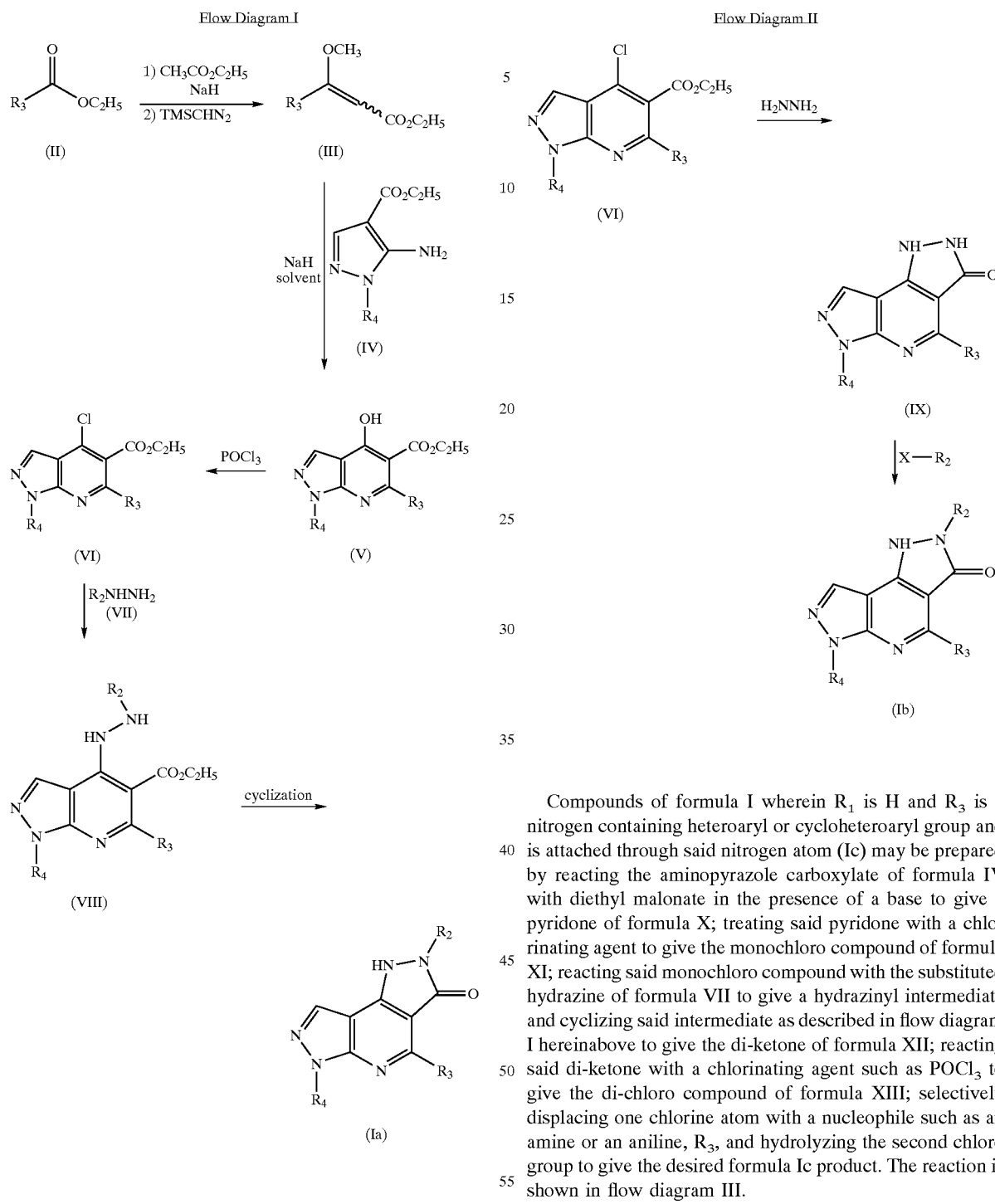

Cyclization of the intermediates of formula VIII is accomplished in the presence of an acid such as acetic acid or a base such as sodium methoxide or sodium hydride. Alternatively, the chloro intermediate of formula VI may be reacted with hydrazine to give the unsubstituted pyrazolone of formula IX and said pyrazolone may be selectively alkylated with an alkyl or benzyl halide to give those compounds of formula I wherein $R_2$ is an optionally substituted alkyl group and $R_1$ is H (Ib). The reaction is shown in flow diagram II, wherein X is Cl, Br or I.

Compounds of formula I wherein $R_1$ is H and $R_3$ is a nitrogen containing heteroaryl or cycloheteroaryl group and is attached through said nitrogen atom (Ic) may be prepared by reacting the aminopyrazole carboxylate of formula IV with diethyl malonate in the presence of a base to give a pyridone of formula X; treating said pyridone with a chlorinating agent to give the monochloro compound of formula XI; reacting said monochloro compound with the substituted hydrazine of formula VII to give a hydrazinyl intermediate and cyclizing said intermediate as described in flow diagram I hereinabove to give the di-ketone of formula XII; reacting said di-ketone with a chlorinating agent such as $POCl_3$ to give the di-chloro compound of formula XIII; selectively displacing one chlorine atom with a nucleophile such as an amine or an aniline, $R_3$, and hydrolyzing the second chloro group to give the desired formula Ic product. The reaction is shown in flow diagram III.

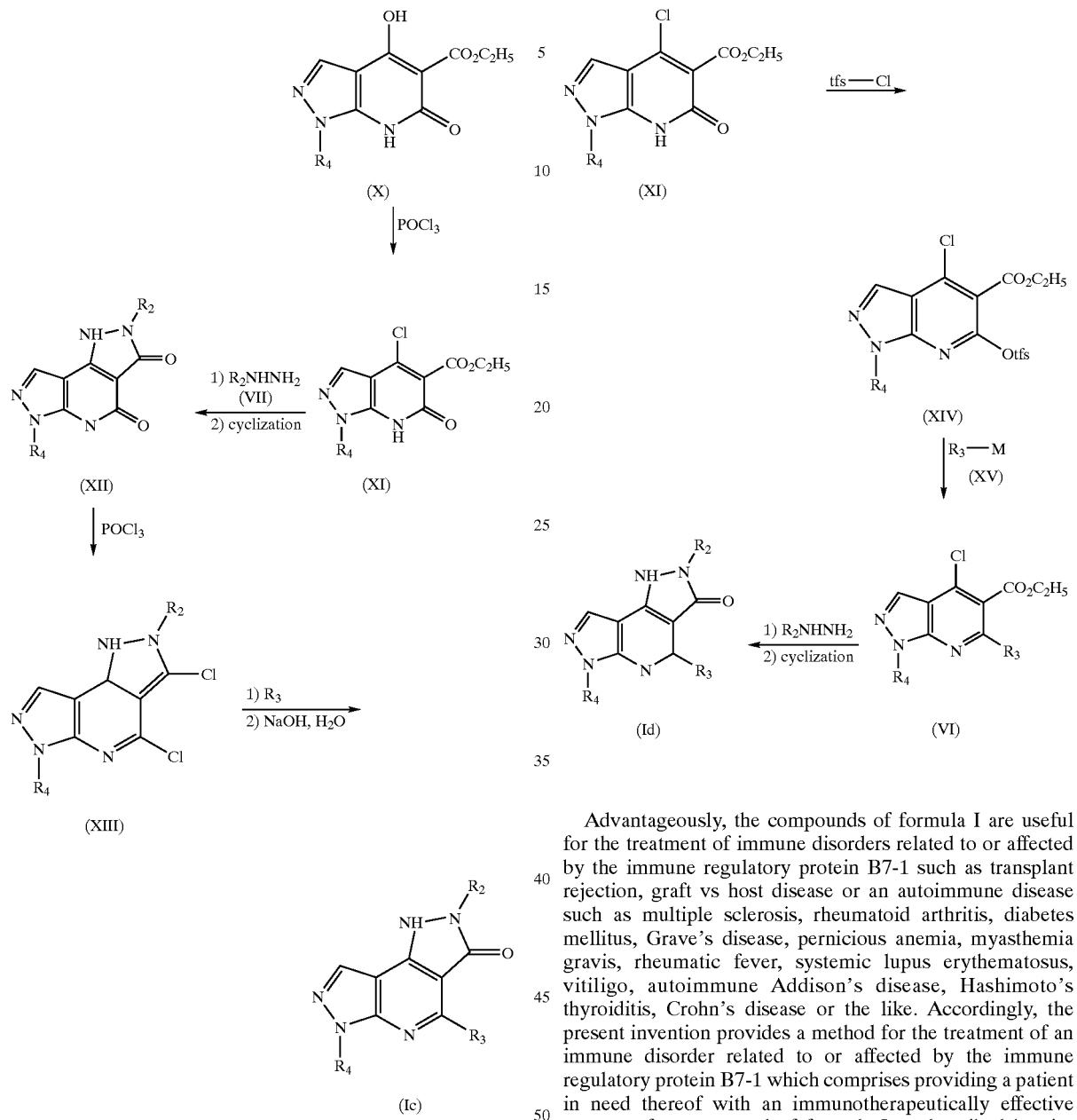

Alternatively, the pyridone intermediate of formula XI may be converted to the trifluoromethylsulfonate of formula XIV via reaction with trifluoromethane sulfonyl (tfs) chloride or tfs anhydride in the presence of a base such as an organic base, i.e. pyridine, triethyl amine or lutidine. The thus-obtained formula XIV compound may undergo an aryl-aryl cross coupling with an aryl boronate or aryl stannate of formula XV in the presence of a catalyst to yield the chloro intermediate of formula VI and said intermediate may then be carried on to those compounds of formula I wherein $R_1$ is H and $R_3$ is aryl (Id) as described hereinabove in flow diagram I. The reaction is shown in flow diagram IV wherein M represents B or Sn.

Advantageously, the compounds of formula I are useful for the treatment of immune disorders related to or affected by the immune regulatory protein B7-1 such as transplant rejection, graft vs host disease or an autoimmune disease such as multiple sclerosis, rheumatoid arthritis, diabetes mellitus, Grave's disease, pernicious anemia, myasthemia gravis, rheumatic fever, systemic lupus erythematosus, vitiligo, autoimmune Addison's disease, Hashimoto's thyroiditis, Crohn's disease or the like. Accordingly, the present invention provides a method for the treatment of an immune disorder related to or affected by the immune regulatory protein B7-1 which comprises providing a patient in need thereof with an immunotherapeutically effective amount of a compound of formula I as described hereinabove. The compounds may be provided by oral or parenteral administration or in any common manner known to be an effective administration of an immunotherapeutic agent to a patient in need thereof.

The term "providing" as used herein with respect to providing a compound or substance embraced by the invention, designates either directly administering such a compound or substance, or administering a prodrug, derivative or analogue which forms an equivalent amount of the compound or substance within the body.

The immunotherapeutically effective amount provided in the treatment of a specific immune disorder may vary according to the specific condition(s) being treated, the size, age and response pattern of the patient, the severity of the disorder, the judgment of the attending physician and the like. In general, effective amounts for daily oral administration may be about 0.01 to 1,000 mg/kg, preferably about 0.5 to 500 mg/kg and effective amounts for parenteral administration may be about 0.1 to 100 mg/kg, preferably about 0.5 to 50 mg/kg.

In actual practice, the compounds of the invention are provided by administering the compound or a precursor thereof in a solid or liquid form, either neat or in combination with one or more conventional pharmaceutical carriers or excipients. Accordingly, the present invention provides a pharmaceutical composition which comprises a pharmaceutically acceptable carrier and an effective amount of a compound of formula i as described hereinabove.

Solid carriers suitable for use in the composition of the invention include one or more substances which may also act as flavoring agents, lubricants, solubilizers, suspending agents, fillers, glidants, compression aides, binders, tablet-disintegrating agents or encapsulating materials. In powders, the carrier may be a finely divided solid which is in admixture with a finely divided compound of formula i. In tablets, the formula i compound may be mixed with a carrier having the necessary compression properties in suitable proportions and compacted in the shape and size desired. Said powders and tablets may contain up to 99% by weight of the formula i compound. Solid carriers suitable for use in the composition of the invention include calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Any pharmaceutically acceptable liquid carrier suitable for preparing solutions, suspensions, emulsions, syrups and elixirs may be employed in the composition of the invention. Compounds of formula I may be dissolved or suspended in a pharmaceutically acceptable liquid carrier such as water, an organic solvent, or a pharmaceutically acceptable oil or fat, or a mixture thereof. Said liquid composition may contain other suitable pharmaceutical additives such as solubilizers, emulsifiers, buffers, preservatives, sweeteners, flavoring agents, suspending agents, thickening agents, coloring agents, viscosity regulators, stabilizers, osmo-regulators, or the like. Examples of liquid carriers suitable for oral and parenteral administration include water (particularly containing additives as above, e.g., cellulose derivatives, preferably sodium carboxymethyl cellulose solution), alcohols (including monohydric alcohols and polyhydric alcohols, e.g., glycols) or their derivatives, or oils (e.g., fractionated coconut oil and arachis oil). For parenteral administration the carrier may also be an oily ester such as ethyl oleate or isopropyl myristate.

Compositions of the invention which are sterile solutions or suspensions are suitable for intramuscular, intraperitoneal or subcutaneous injection. Sterile solutions may also be administered intravenously. Inventive compositions suitable for oral administration may be in either liquid or solid composition form.

For a more clear understanding, and in order to illustrate the invention more clearly, specific examples thereof are set forth hereinbelow. The following examples are merely illustrative and are not to be understood as limiting the scope and underlying principles of the invention in any way.

The term HNMR designates proton nuclear magnetic resonance. The terms EtOAc, THF and DMF designate ethyl acetate, tetrahydrofuran and dimethyl formamide, respectively. All chromatography is performed using $SiO_2$ as support.

EXAMPLE 1

Preparation of Ethyl 3-Methoxy-3-(5-bromo-3-pyridinyl)-2-propenoate

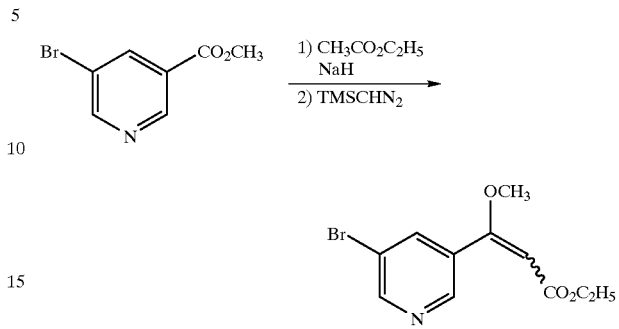

A solution of methyl 5-bromonicotinate (15.0 g, 69.4 mmol) in ethyl acetate is treated with NaH (60% in mineral oil, 2.4 g) and gently heated at 40° C. until a mild exotherm occurs. After cessation of reflux, the reaction mixture is treated with additional NaH (2.27 g, 139 mmol total), heated at reflux temperature for 16 h, cooled to room temperature and diluted with $CH_2Cl_2$ and water. The organic phase is separated, washed with brine, dried over $Na_2SO_4$ and concentrated in vacuo. The resultant oil is dissolved in acetonitrile and methanol, treated with a 2M solution of trimethylsilyl diazomethane ($TMSCHN_2$) in hexanes (70 ml, 140 mmol), stirred for 36 h and treated with 5% aqueous HCl. After cessation of nitrogen evolution, the phases are separated and the organic phase is washed with brine, dried over $Na_2SO_4$ and concentrated in vacuo. The resultant residue is chromatographed through a plug of silica gel (4:1 hexanes:EtOAc) to give the title compound as a light brown solid, 10.1 g (53% yield), identified by HNMR and mass spectral analyses.

EXAMPLE 2

Preparation of Ethyl 4-Chloro-6-(5-bromo-3-pyridinyl)-1-methyl-5-pyrazolopyridinecarboxylate

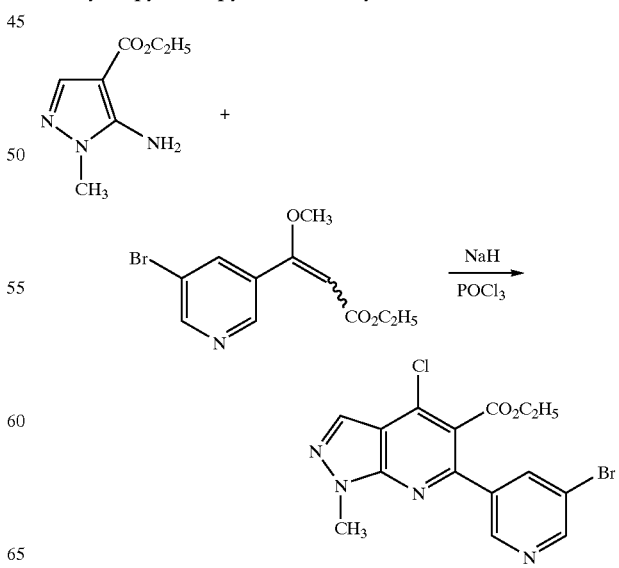

A solution of ethyl 5-amino-1-methyl-4-pyrazole carboxylate (5.91 g, 35 mmol) in THF is treated with NaH (60% in mineral oil, 4.1 g, 122 mmol), stirred for 0.5 h, treated with ethyl 3-methoxy-3-(5-bromo-3-pyridinyl)-2-propenoate (10.0 g, 35 mmol), heated at reflux temperature for 36 h, cooled to 0° C., acidified to pH 5 with aqueous HCl and extracted with EtOAc. The combined extracts are washed with brine, dried over $Na_2SO_4$ and concentrated in vacuo. The resultant residue is triturated with hexanes to give the 4-hydroxy precursor of the title product as a white solid, 9 g, identified by HNMR. This solid is dissolved in $POCl_3$ (150 mL), heated at reflux temperature for 2 h and concentrated in vacuo. The resultant residue is dissolved in EtOAc, cooled to 0° C. and neutralized with aqueous $NaHCO_3$. The organic phase is separated, washed with brine, dried over $Na_2SO_4$ and concentrated in vacuo. This residue is chromatographed on silica gel (3:1 hexanes:EtOAc) to give the title product as a white powder, 7.43 g (65% yield over 2 steps), identified by HNMR and mass spectral analyses.

EXAMPLE 3

Preparation of Ethyl 4-[N'-(3-Fluorophenyl)hydrazino]-1-methyl-6-(5-bromo-3-pyridinyl)-1H-pyrazolo[3,4-b]pyridine-5-carboxylate

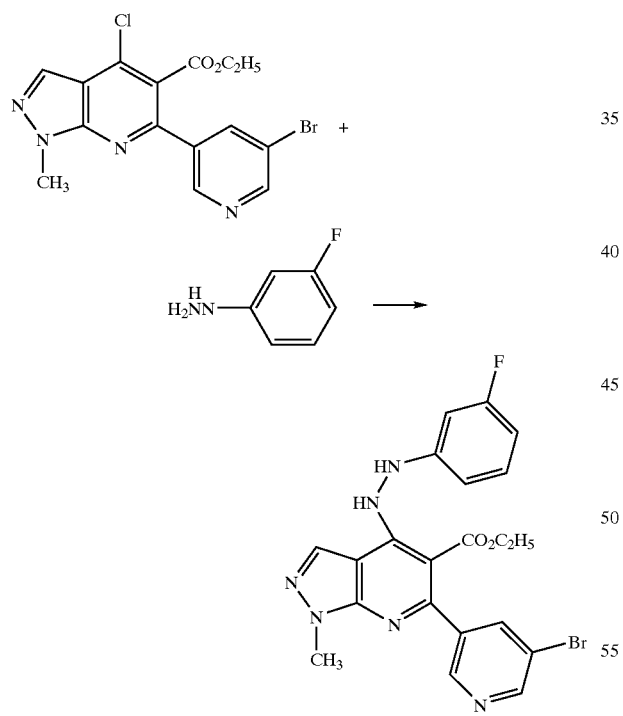

A solution of ethyl 4-chloro-6-(5-bromo-3-pyridinyl)-1-methyl-5-pyrazolopyridinecarboxylate (1.3 g, 3.28 mmol) in ethanol is treated with 3-fluorophenylhydrazine (1.03 g, 8.2 mmol), heated at reflux temperature for 6 h and concentrated in vacuo. The resultant residue is chromatographed (silica gel, 1:1 hexanes:EtOAc) to afford the title product as a white foam, 1.1 g (69% yield), identified by HNMR and mass spectral analyses.

EXAMPLE 4

Preparation of 4-(5-Bromo-3-pyridinyl)-2-(3-fluorophenyl)-6-methyl-1,6-dihydrodipyrazalo[3,4-b:3,4-d]pyridin-3(2H)-one

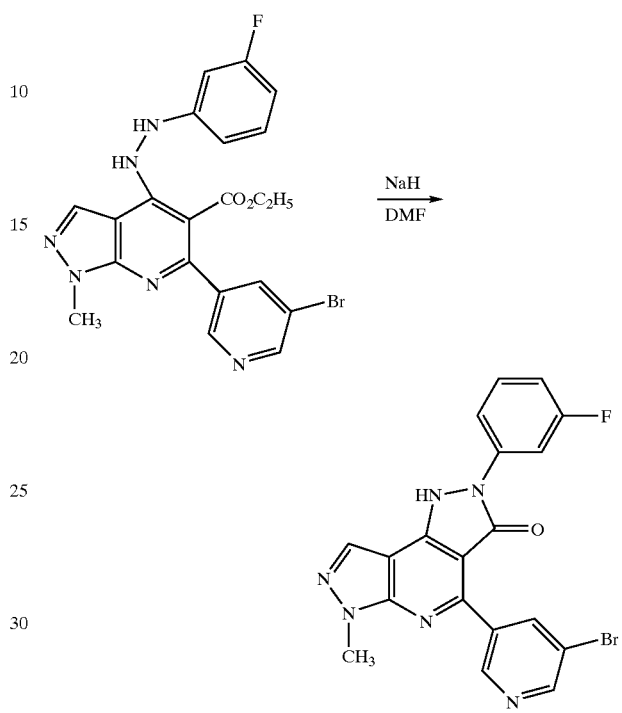

A solution of ethyl 4-[N'-(3-fluorophenyl)hydrazino]-1-methyl-6-(5-bromo-3-pyridinyl)-1H-pyrazolo[3,4-b]pyridine-5-carboxylate (1.0 g, 2.11 mmol) in DMF is treated with NaH (0.15 g, 8.75 mmol) heated at 90° C. for 12 h, poured into ice water, acidified to pH 3 with aqueous HCl and filtered. The filtercake is washed with cold EtOAc and air-dried to afford the title product as an off-white solid, 0.8 g, (93% yield), identified by HNMR and mass spectral analyses.

EXAMPLE 5

Preparation of 4-(3-Fluorophenyl)-2-(4-chlorophenyl)-6-methyl-1,6-dihydrodipyrazolo[3,4-b:3,4-d]pyridin-3(2H)-one

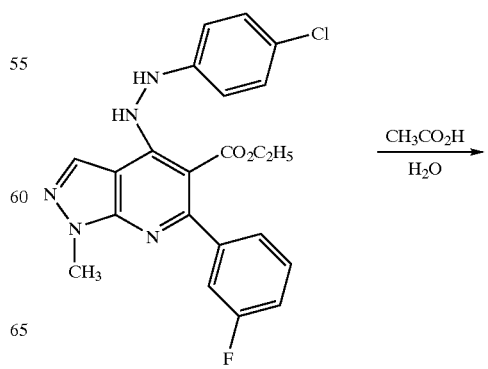

EXAMPLES 6–68

Preparation of Dihydrodipyrazolopyridinone Compounds

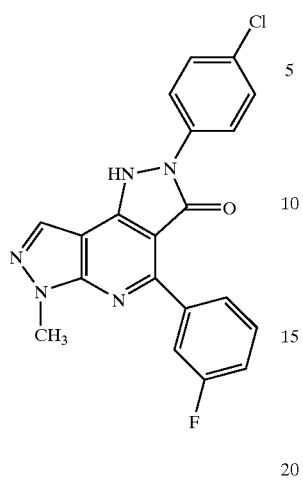

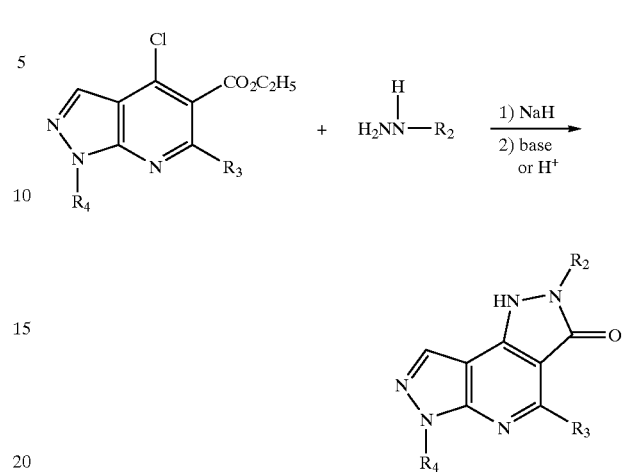

A mixture of ethyl 4-[N'-(4-chlorophenyl)hydrazino]1-methyl-6-(3-fluorophenyl)-1H-pyrazolo[3,4-b]pyridine carboxylate (0.15 g, 2.27 mmol) in acetic acid is heated at 90° C. for 12 h, poured into ice water and filtered. The filtercake is washed with cold EtOAc and air-dried to give the title product as an off-white solid (0.024 g (19% yield), identified by HNMR and mass spectral analyses.

Using essentially the same procedures described in Examples 1–5 hereinabove and employing the appropriate 4-chloro-5-pyrazolopyridinecarboxylate substrate and aryl hydrazine reagent, the compounds shown in Table I are obtained and identified by HNMR and mass spectral analyses.

TABLE I

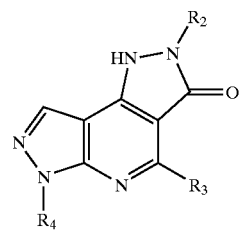

| Ex No. | R2 | R3 | R4 | [M + H] |
|---|---|---|---|---|
| 6 | 4-Cl—$C_6H_4$ | $C_6H_5$ | $CH_3$ | 375.817 |
| 7 | 3-F—$C_6H_4$ | 3-$CF_3$—$C_6H_4$ | $C_6H_5$ | 489.4318 |
| 8 | 4-F—$C_6H_4$ | 5-Bromo-3-pyridinyl | $CH_3$ | 439.2465 |
| 9 | 2-pyridinyl | 5-Bromo-3-pyridinyl | $CH_3$ | 422.2439 |
| 10 | 2-pyridinyl | 3-$CH_3$—$C_6H_4$ | $CH_3$ | 356.3869 |
| 11 | 3-$CH_3$-5-$CF_3$—$C_6H_3$ | 3-$CH_3$—$C_6H_4$ | $CH_3$ | 437.4242 |
| 12 | 3-$CH_{3\text{-}5\text{-}CF3}$—$C_6H_3$ | 3-Br—$C_6H_4$ | $CH_3$ | 502.2934 |
| 13 | 2-pyridinyl | 3-Br—$C_6H_4$ | $CH_3$ | 421.2561 |
| 14 | 2-pyridinyl | 5-methyl-3-pyridinyl | $CH_3$ | 357.3747 |
| 15 | 3-$CH_{3\text{-}5\text{-}CF3}$—$C_6H_3$ | 5-methyl-3-pyridinyl | $CH_3$ | 438.412 |
| 16 | 4-I—$C_6H_4$ | 3-$CF_3$—$C_6H_4$ | $CH_3$ | 535.267 |
| 17 | 3,5-di-$CH_3$—$C_6H_3$ | 3-Br—$C_6H_4$ | $CH_3$ | 448.322 |
| 18 | 4-$NO_2$—$C_6H_4$ | 3-Br—$C_6H_4$ | $CH_3$ | 465.2659 |
| 19 | 3,5-di-$CH_3$—$C_6H_3$ | 3-$CH_3$—$C_6H_4$ | $CH_3$ | 383.4528 |
| 20 | 3,5-di-$CH_3$—$C_6H_3$ | 3-$CF_3$—$C_6H_4$ | $CH_3$ | 437.4242 |
| 21 | 3-$CO_2H$—$C_6H_4$ | 3-$CF_3$—$C_6H_4$ | $CH_3$ | 453.3803 |
| 22 | 3-$CO_2CH_3$—$C_6H_4$ | 3-$CF_3$—$C_6H_4$ | $CH_3$ | 467.4071 |
| 23 | 6-ethoxy-3-pyridazinyl | 3-$CF_3$—$C_6H_4$ | $CH_3$ | 455.3992 |
| 24 | 6-oxo-1,6-dihydro-3-pyridazinyl | 3-$CF_3$—$C_6H_4$ | $CH_3$ | 427.3455 |
| 25 | 3-$CO_2H$-4-Cl—$C_6H_3$ | 3-$CF_3$—$C_6H_4$ | $CH_3$ | 487.825 |
| 26 | 3-$CO_2CH_3$-4-Cl—$C_6H_3$ | 3-$CF_3$—$C_6H_4$ | $CH_3$ | 501.8519 |
| 27 | 3,5-di-$CH_3$—$C_6H_3$ | 5-methyl-2-pyridyl | $CH_3$ | 384.4406 |
| 28 | 3-$CO_2C_2H_5$—$C_6H_4$ | 3-$CF_3$—$C_6H_4$ | $CH_3$ | 481.434 |

TABLE I-continued

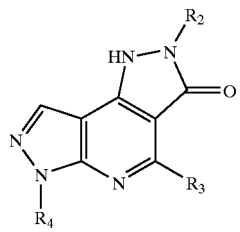

| Ex No. | R2 | R3 | R4 | [M + H] |
|---|---|---|---|---|
| 29 | 3-Cl-4-CO$_2$CH$_3$—C$_6$H$_3$ | 3-CF$_3$—C$_6$H$_4$ | CH$_3$ | 501.8519 |
| 30 | 3-Cl-4-CO$_2$H—C$_6$H$_3$ | 3-CF$_3$—C$_6$H$_4$ | CH$_3$ | 487.825 |
| 31 | 3-Cl-4-CO$_2$CH$_3$—C$_6$H$_3$ | 3-Br—C$_6$H$_4$ | CH$_3$ | 512.7497 |
| 32 | 3-Cl-4-CO$_2$H—C$_6$H$_3$ | 3-Br—C$_6$H$_4$ | CH$_3$ | 498.7228 |
| 33 | 4-CO$_2$H—C$_6$H$_4$ | 3-CF$_3$—C$_6$H$_4$ | CH$_3$ | 453.3803 |
| 34 | 4-CO$_2$CH$_3$—C$_6$H$_4$ | 3-CF$_3$—C$_6$H$_4$ | CH$_3$ | 467.4071 |
| 35 | 3-CO$_2$CH$_{3\text{-}4\text{-}F\text{-}}$C$_6$H$_3$ | 3-CF$_3$—C$_6$H$_4$ | CH$_3$ | 485.3976 |
| 36 | 3-CO$_2$H-4-F—C$_6$H$_3$ | 3-CF$_3$—C$_6$H$_4$ | CH$_3$ | 471.3707 |
| 37 | 3-F-4-CO$_2$CH$_3$—C$_6$H$_3$ | 3-CF$_3$—C$_6$H$_4$ | CH$_3$ | 485.3976 |
| 38 | 3-F-4-CO$_2$H—C$_6$H$_3$ | 3-CF$_3$—C$_6$H$_4$ | CH$_3$ | 471.3707 |
| 39 | 4-F—C$_6$H$_4$ | 3-CF$_3$—C$_6$H$_4$ | CH$_3$ | 427.3609 |
| 40 | 4-NO$_2$—C$_6$H$_4$ | 3-CF$_3$—C$_6$H$_4$ | CH$_3$ | 454.3681 |
| 41 | 2-F—C$_6$H$_4$ | 3-CF$_3$—C$_6$H$_4$ | CH$_3$ | 427.3609 |
| 42 | 4-t-Bu-C$_6$H$_4$ | 3-CF$_3$—C$_6$H$_4$ | CH$_3$ | 465.478 |
| 43 | 3-F—C$_6$H$_4$ | 3-CF$_3$—C$_6$H$_4$ | CH$_3$ | 427.3609 |
| 44 | 2,4-di-F—C$_6$H$_3$ | 3-CF$_3$l—C$_6$H$_4$ | CH$_3$ | 445.3514 |
| 45 | 4-CF$_3$-2-pyrimidinyl | 3-CF$_3$—C$_6$H$_4$ | CH$_3$ | 479.3443 |
| 46 | 4-F—C$_6$H$_4$ | 3-NO$_2$—C$_6$H$_4$ | CH$_3$ | 404.3603 |
| 47 | 4-F—C$_6$H$_4$ | 3-NH$_2$—C$_6$H$_4$ | CH$_3$ | 374.3773 |
| 48 | 4-NH$_2$—C$_6$H$_4$ | 3-CF$_3$—C$_6$H$_4$ | CH$_3$ | 424.3851 |
| 49 | 3-F—C$_6$H$_4$ | 3-pyridyl | CH$_3$ | 360.3505 |
| 50 | 3-F—C$_6$H$_4$ | 3-NO$_2$—C$_6$H$_4$ | CH$_3$ | 404.3603 |
| 51 | 2-CO$_2$C$_2$H$_5$-4-CH$_3$-3-thienyl | 3-CF$_3$—C$_6$H$_4$ | CH$_3$ | 501.489 |
| 52 | 2-CO$_2$H-4-CH$_3$-3-thienyl | 3-CF$_3$—C$_6$H$_4$ | CH$_3$ | 473.4353 |
| 53 | 3-F—C$_6$H$_4$ | 3-CN—C$_6$H$_4$ | CH$_3$ | 384.3725 |
| 54 | 3-F—C$_6$H$_4$ | 3-CONH$_2$—C$_6$H$_4$ | CH$_3$ | 402.3877 |
| 55 | 3-F—C$_6$H$_4$ | 3-CH$_3$SO$_2$—C$_6$H$_4$ | CH$_3$ | 437.4543 |
| 56 | 3-F—C$_6$H$_4$ | 3-CH$_3$SO—C$_6$H$_4$ | CH$_3$ | 421.4529 |
| 57 | 4-biphenyl | 3-CF$_3$—C$_6$H$_4$ | CH$_3$ | 485.4682 |
| 58 | 4-benzyloxyphenyl | 3-CF$_3$—C$_6$H$_4$ | CH$_3$ | 515.4945 |
| 59 | 3-benzyloxyphenyl | 3-CF$_3$—C$_6$H$_4$ | CH$_3$ | 515.4945 |
| 60 | 3-F—C$_6$H$_4$ | 3-CO$_2$H—C$_6$H$_4$ | CH$_3$ | 403.3725 |
| 61 | H | 3-CF$_3$—C$_6$H$_4$ | CH$_3$ | 410.36 |
| 62 | benzyl | 3-CF$_3$—C$_6$H$_4$ | CH$_3$ | 423.3973 |
| 63 | 4-CO$_2$CH$_3$—C$_6$H$_4$—CH$_2$ | 3-CF$_3$—C$_6$H$_4$ | CH$_3$ | 481.434 |
| 64 | 4-F-C$_6$H$_4$ | 3-CF$_3$—C$_6$H$_4$ | benzyl | 503.4587 |
| 65 | 4-F-C$_6$H$_4$ | 3-CF$_3$—C$_6$H$_4$ | H | 414.09 |
| 66 | 4-F-C$_6$H$_4$ | 3-CF$_3$—C$_6$H$_4$ | HOCH$_2$CH$_2$ | 458.12 |
| 67 | 4-F-C$_6$H$_4$ | 3-CF$_3$—C$_6$H$_4$ | C$_2$H$_5$ | 441.3878 |
| 68 | 4-F-C$_6$H$_4$ | 3-CF$_3$—C$_6$H$_4$ | n-C$_3$H$_7$ | 455.4147 |

EXAMPLE 69

Preparation of Ethyl 4-Hydroxy-1-methyl-6-oxo-6,7-dihydro-1H-pyrazolo-[3,4-b]pyridine-5-carboxylate

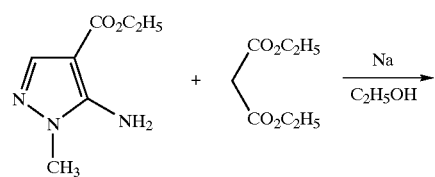

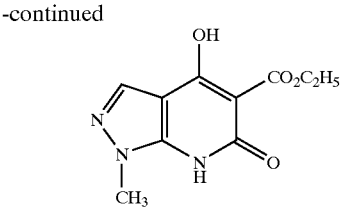

A solution of sodium metal (12.7 g, 0.55 mol) in ethanol is treated at room temperature with ethyl 5-amino-1-methyl-4-pyrazolecarboxylate (25 g, 0.148 mol), stirred for 0.5 h, treated dropwise with a solution of diethyl malonate (80 mL, 0.52 mol in ethanol over a 0.5 h period, heated at reflux temperature for 56 h, cooled to room temperature, diluted with water, washed with ethyl acetate, acidified to pH 2 with HCl and filtered. The filtercake is washed sequentially with water, ethanol, ethyl acetate and toluene and dried in vacuo at 40° C. for 16 h to afford the title product as a white solid, 28.7 g (82% yield), identified by HNMR analysis.

EXAMPLE 70
Preparation of Ethyl 4-chloro-1-methyl-6-oxo-6,7-dihydro-1H-pyrazolo-[3,4-b]pyridine-5-carboxylate

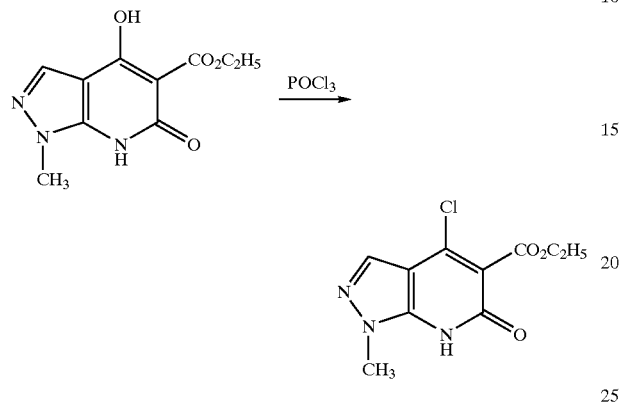

A solution of ethyl 4-hydroxy-1-methyl-6-oxo-6,7-dihyrdo-1H-pyrazolo-[3,4-b]pyridine-5-carboxylate (10 g, 42.2 mmol) in acetonitrile is treated with benzyl triethyl ammonium chloride (40.4 g, 169 mmol), followed by phosphorous oxychloride (17.6 mL, 190 mmol), heated at 40° C. for 0.5 h, then at reflux temperature for 2.5 h, cooled to room temperature, diluted with water (caution exotherm), stirred at ambient temperatures for 16 h and filtered. The filtercake is washed with cyclohexane and dried in vacuo to give the title compound as a white solid, 7.87 g (73% yield), identified by HNMR analysis.

EXAMPLE 71
Preparation of Ethyl 4-Chloro-1-methyl-6-trifluoromethanesulfonyloxy-1H-pyrazolo[3,4-b]pyridine-5-carboxylate

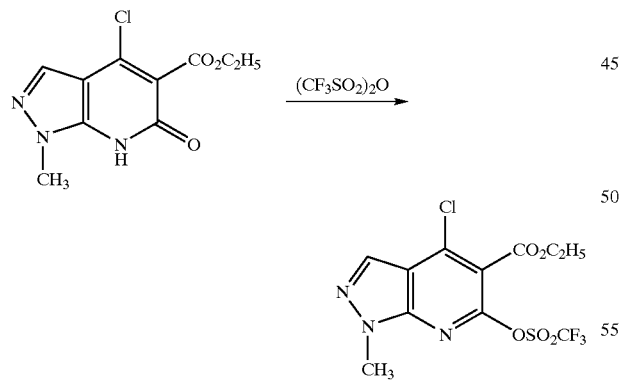

A solution of ethyl 4-chloro-1-methyl-6-oxo-6,7-dihydro-1H-pyrazolo-[3,4-b]pyridine-5-carboxylate (2.56 g, 10 mmol) in methylene chloride and 2,6-di-t-butyl-4-methylpyridine (3.07 g, 15 mmol is cooled to −78° C., treated dropwise with a solution of trifluoromethane sulfonic anhydride (3.30 mL, 18 mmol) in CH$_2$Cl$_2$, stirred at 0° C. for 4 h and diluted with EtOAc. The reaction mixture is washed sequentially with saturated NaHCO$_3$, water, 10% aqueous HCl, water and brine, dried over Na$_2$SO$_4$ and concentrated in vacuo to give the title product as a tan oil, 3.56 g (92% yield), identified by HNMR.

EXAMPLE 72
Preparation of Ethyl 4-Chloro-6-(3,5-dichlorophenyl)-1-methyl-1H-pyrazolo-[3,4-b]pyridine-5-carboxylate

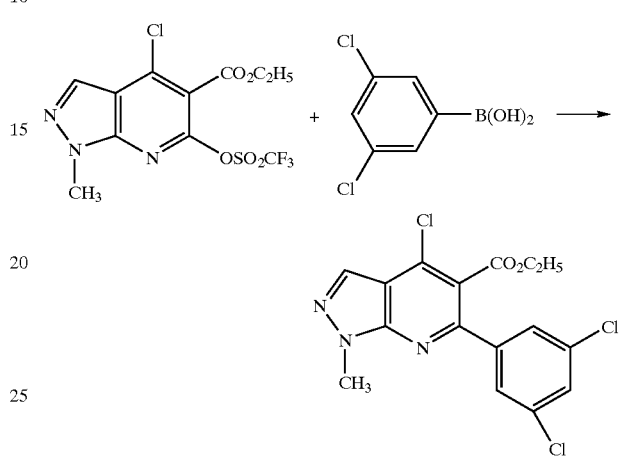

A solution of ethyl 4-chloro-1-methyl-6-trifluoromethanesulfonyloxy-1H-pyrazolo[3,4-b]pyridine-5-carboxylate (387 mg, 1 mmol) in THF is treated with tetrakis(triphenyl phosphine) palladium (115 mg, 10 mol %), stirred for 20 min at room temperature, treated sequentially with 3,5-dichlorobenzeneboronic acid (285 mg, 1.5 mmol), 2N K$_2$CO$_3$ (0.7 mL) and benzyl triethyl ammonium chloride (319 mg, 1.4 mmol), heated at reflux temperature for 4 h, cooled to room temperature and diluted with EtOAc. The phases are separated and the organic phase is washed sequentially with water and brine, dried over Na$_2$SO$_4$ and concentrated in vacuo. The resultant residue is chromatographed (silica gel, hexanes:EtOAc, 5:1) to afford the title product as a white solid, 127 mg (33% yield), identified by HNMR analysis.

EXAMPLE 73
Preparation of 4-(3,5-Dichlorophenyl)-2-(3-fluorophenyl)-6-methyl-1,6-dihydrodypyrazolo[3,4-b:3',4'-d]pyridin-3(2H)-one

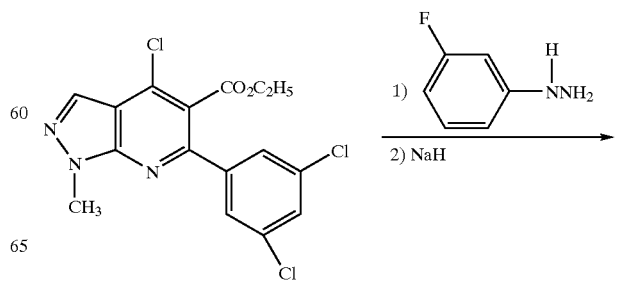

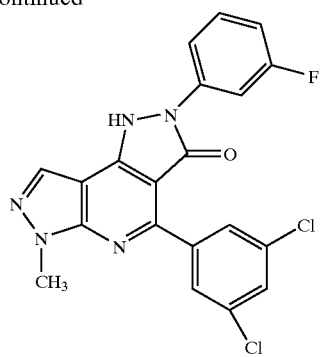

A solution of ethyl 4-chloro-6-(3,5-dichlorophenyl)-1-methyl-1H-pyrazolo-[3,4-b]pyridine-5-carboxylate (120 mg, 0.31 mmol) in DMF is treated with 3-fluoro-phenyl hydrazine (99 mg, 0.78 mmol), heated at 100° C. for 10 h, cooled to room temperature, diluted with water and EtOAc and filtered. The filtercake is air-dried to afford the 4-hydrazinyl intermediate as an off-white solid, 80 mg. This solid (65 mg, 0.13 mmol) is suspended in DMF, treated with NaH (14 mg, 0.41 mmol), stirred at 100° C. for 3 h, cooled to room temperature, diluted with EtOAc and filtered. The filtercake is air-dried to afford the title product as a pink solid, 44 mg (33% yield), identified by HNMR and mass spectral analyses.

EXAMPLES 74–77
Preparation of Dihydrodipyrazolopyridinone Compounds

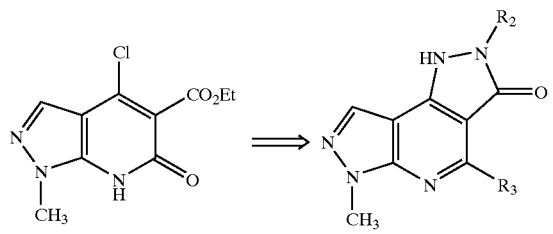

Using essentially the same procedures described in Examples 73–76 hereinabove and employing the appropriate arylboronic acid and aryl hydrazine as reagents, the compounds shown in Table II are obtained and identified by HNMR and mass spectral analyses.

TABLE II

| Ex No. | R2 | R3 | [M + H] |
|---|---|---|---|
| 74 | 3-F—$C_6H_4$ | 3-thienyl | 366.0826 |
| 75 | 3-F—$C_6H_4$ | 3-$CH_3O$—$C_6H_4$ | 390.13 |
| 76 | 3-F—$C_6H_4$ | 1,3-benzodioxol-5-yl | 404.11 |
| 77 | 3-F—$C_6H_4$ | 2-fluoro-1,1'-biphen-4-yl | 454.1481 |

EXAMPLE 78
Preparation of 2-(3-Fluorophenyl)-6-methyl-1,2,5,6-tetrahydro-1,2,5,6,7-pentaza-as-indacene-3,4-dione

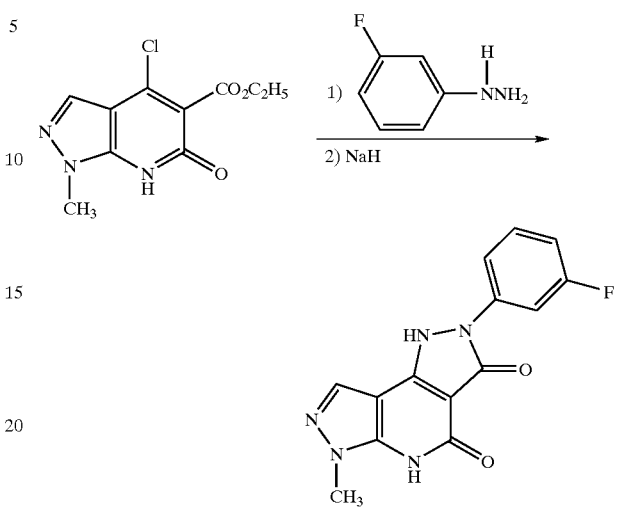

A suspension of ethyl 4-chloro-1-methyl-6-trifluoromethanesulfonyloxy-1H-pyrazolo[3,4-b]pyridine-5-carboxylate (524 mg, 2.05 mmol) in toluene is treated with 3-fluorophenyl hydrazine (651 mg, 5.13 mmol) and a catalytic amount of 2,6-di-t-butyl-4-methylpyridine, heated at reflux temperature for 36 h, cooled to room temperature and filtered. The filtercake is washed with cold toluene and dried in vacuo to give the 4-hydrazinyl intermediate as a white powder, 624 mg (88% yield). This white powder (550 mg, 1.59 mmol) is suspended in THF, treated with NaH (60% in oil, 187 mg, 5.58 mmol), heated at reflux temperature for 24 h, cooled to room temperature, quenched carefully with 10% HCl, diluted with EtOAc and filtered. The filtercake is washed sequentially with water and EtOAc and air-dried to afford the title product as a white powder, 391 mg (83% yield, 73% yield over 2 steps), identified by HNMR and mass spectral analyses.

EXAMPLE 79
Preparation of 3-Chloro-4-chloro-2-(3-fluorophenyl)-6-methyl-2,6-dihydropyrazolo[3,4-b:3',4'-d] pyridine

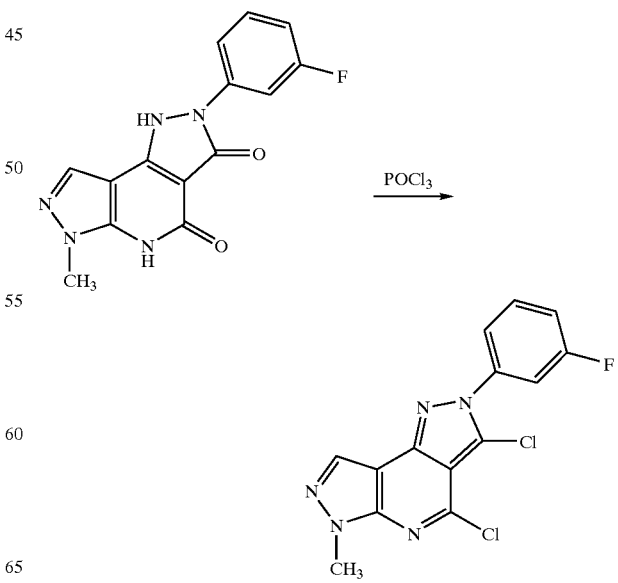

A mixture of 2-(3-fluorophenyl)-6-methyl-1,2,5,6-tetrahydro-1,2,5,6,7-pentaza-as-indacene-3,4-dione (1.5 g, 5.02 mmol) and phosphorousoxychloride (20 mL) is heated at reflux temperature for 5 h, cooled to room temperature and concentrated in. vacuo. The resultant residue is diluted with ice water, neutralized with $Na_2CO_3$ and extracted with EtOAc. The extracts are combined, dried over $Na_2SO_4$ and concentrated in vacuo to afford the title product as a light yellow solid, 1.2 g (75% yield), identified by HNMR and mass spectral analyses.

EXAMPLE 80

Preparation of 3-Chloro-4-(2-6-dimethyl-4-morpholinyl)-2-(3-fluorophenyl)-6-methyl-2,6-dihydrodipyrazolo[3,4-b:3',4'-d]pyridine

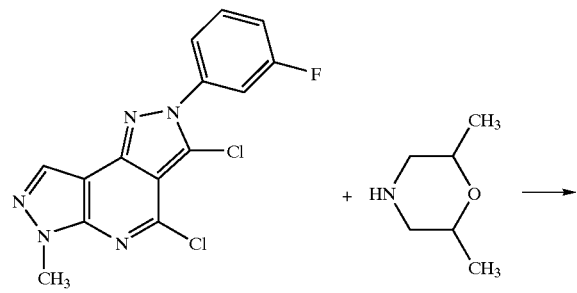

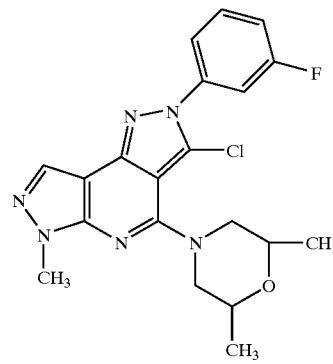

A mixture of 3-chloro-4-chloro-2-(3-fluorophenyl)-6-methyl-2,6-dihydropyrazolo[3,4-b:3',4'-d) pyridine (100 mg, 0.315 mol) and 2,6-dimethylmorpholine (0.097 mL, 0.787 mmol) in DMF is heated at 140° C. for 4 h, cooled to room temperature, quenched with water, acidified to pH 3 with 3NHCl and extracted with EtOAc. The extracts are combined, dried over $Na_2SO_4$ and concentrated in vacua. The resultant resdue is purified by flash chromatography (silica gel, 0.5% methanol in chloroform) to afford the title product as a yellow solid, 90 mg (69% yield), mp 194.5–197° C., identified by HNMR and mass spectral analyses.

EXAMPLE 81

Preparation of 4-(2,6-Dimethyl-4-morpholinyl)-2-(3-fluorophenyl)-6-methyl-1,6-dihydrodipyrazolo[3,4-b:3'-4'-d]pyridin-3(2H)-one

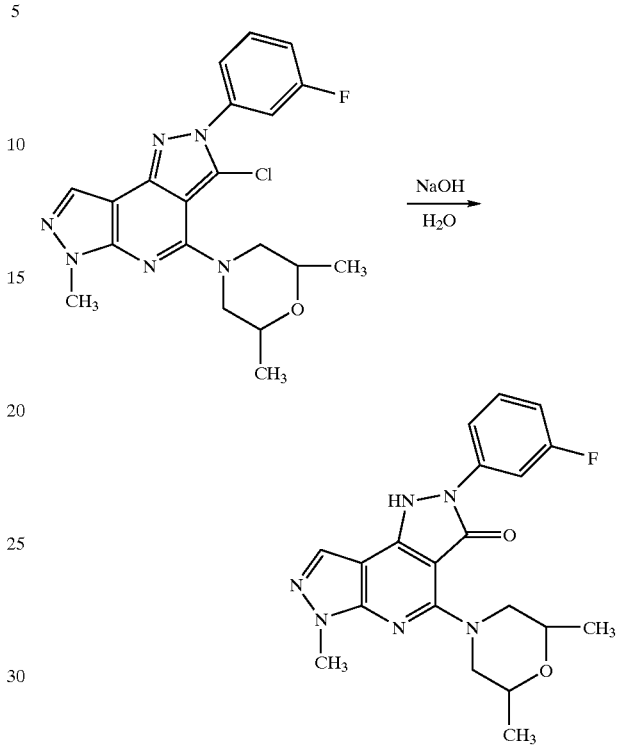

A solution of 3-chloro-4-(2-6-dimethyl-4-morpholinyl)-2-(3-fluorophenyl)-6-methyl-2,6-dihydrodipyrazolo[3,4-b:3',4'-d]pyridine (48 mg, 0.116 mmol) in 3:1 methanol:THF is treated with 0.4 mL of 4N $NaOH_2$, heated at reflux temperature for 16 h, cooled to room temperature, quenched with 3N HCl and extracted with EtOAc. The extracts are combined, dried over $Na_2SO_4$ and concentrated in vacuo to afford the title product as a beige powder, 40 mg (87% yield), mp 204.7–207° C., identified by HNMR and mass spectral analyses.

EXAMPLE 82

Evaluation of B7-1/CD28 Binding Inhibition for Test Compounds

CD28/B7-1 ELISA

Wells are coated with 300 ng CD28-Fc in carbonate buffer (pH 9.4) overnight at 4° C., blocked with 1% bovine serum albumin in tris-buffered saline (TBS) for 1 h at 22° C. and washed 3 times in TBS prior to assay. The detection complex is formed as follows: B7-1-Fc-biotin, prepared using NHS-LC-biotin (Pierce #21335) according to the manufacturers instructions (4.1 moles biotin/mole Fc), is added at 0.8 ug/ml to streptavidin-alkaline phosphatase (Caltag Sa1008 at 1:1000 in TBS. Gradient dilutions of test compound in dimethylsulfoxide (1% final) are added to this complex and incubated 30 min. at 22° C. Detection complex (+/− inhibitors) is then added to the CD28 coated wells for 25 min. at 22° C., washed 5 times with TBS, developed with the calorimetric substrate pNPP (Pierce #34045) in diethanolamine/$MgCl_2$ buffer (pH 9.5) and read at 405 nm. The inhibition constant ($IC_{50}$) is calculated by subtracting background binding and comparing to uninhibited (DMSO alone) controls. The inhibition constant represents the concentration of test compound required to achieve 50% inhibition. The results are shown in Table III.

TABLE III

| Example Number | B7-1/CD28 Inhibition IC50 (nM) |
|---|---|
| 4 | 20 |
| 5 | 3000 |
| 6 | 1800 |
| 7 | 750 |
| 8 | 200 |
| 9 | 400 |
| 10 | 150 |
| 11 | 3000 |
| 12 | 190 |
| 13 | 70 |
| 14 | 3000 |
| 15 | 3000 |
| 16 | 50 |
| 17 | 58 |
| 18 | 12 |
| 19 | 990 |
| 20 | 66 |
| 21 | 48 |
| 22 | 8 |
| 23 | 290 |
| 24 | 72 |
| 25 | 7 |
| 26 | 120 |
| 27 | 3000 |
| 28 | 170 |
| 29 | 41 |
| 30 | 16 |
| 31 | 9 |
| 32 | 9 |
| 33 | 190 |
| 34 | 31 |
| 35 | 98 |
| 36 | 70 |
| 37 | 12 |
| 38 | 210 |
| 39 | 50 |
| 40 | 100 |
| 41 | 400 |
| 42 | 900 |
| 43 | 20 |
| 44 | 1000 |
| 45 | 1200 |
| 46 | 50 |
| 47 | 400 |
| 48 | 50 |
| 49 | 3000 |
| 50 | 4 |
| 51 | 2100 |
| 52 | 1700 |
| 53 | 30 |
| 54 | 1500 |
| 55 | 1900 |
| 56 | 330 |
| 57 | 39 |
| 58 | 25 |
| 59 | 20 |
| 60 | 70 |
| 61 | 200 |
| 62 | 3000 |
| 63 | 3000 |
| 64 | 70 |
| 65 | 50 |
| 66 | 800 |
| 67 | 780 |
| 68 | 90 |
| 73 | 40 |
| 74 | 105 |
| 75 | 82 |
| 76 | 295 |
| 77 | 3000 |
| 81 | 188 |

What is claimed is:

1. A compound of formula I

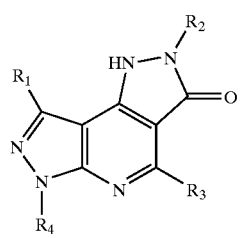

wherein $R_1$ and $R_4$ are each independently H, $C_1$–$C_{10}$alkyl optionally substituted with one or more halogen, hydroxy, $C_1$–$C_4$alkoxy, $CO_2R_6$, $CONR_7R_8$, $C_3$–$C_7$cycloalkyl or optionally substituted phenyl groups, or phenyl optionally substituted with one to three halogen, hydroxy, $C_1$–$C_6$haloalkyl, $C_1$–$C_4$alkoxy, $CO_2R_9$, $NR_{10}R_{11}$ or CN groups;

$R_2$ is H, $C_1$–$C_6$alkyl optionally substituted with a phenyl, naphthyl or 5- to 10-membered heteroaryl ring system containing 1, 2 or 3 heteroatoms selected from N, O or S group each group optionally substituted with one to three $C_1$–$C_6$alkyl, $C_1$–$C_6$haloalkyl, $C_1$–$C_4$alkoxy, hydroxy, CHO, $NO_2$, CN, $CO_2R_{12}$ or $NR_{13}R_{14}$ groups, phenyl optionally substituted with one to three halogen, $NO_2$, CN, hydroxy, $C_1$–$C_6$alkyl, $C_1$–$C_6$haloalkyl, $C_1$–$C_6$alkoxy, phenyl, phenoxy, benzyl, benzyloxy, $CO_2R_{17}$, $NR_{18}R_{19}$ or $CH_2CO_2R_{20}$ groups, naphthyl optionally substituted with one to three halogen, $NO_2$, CN, hydroxy, $C_1$–$C_6$alkyl, $C_1$–$C_6$haloalkyl, $C_1$–$C_6$alkoxy, phenyl, phenoxy, benzyl, benzyloxy, $CO_2R_{17}$, $NR_{18}R_{19}$ or $CH_2CO_2R_{20}$ groups, $C_5$–$C_7$cycloheteroalkyl optionally substituted with one to three halogen, $NO_2$, CN, $C_1$–$C_6$alkyl, $C_1$–$C_6$haloalkyl, $C_1$–$C_4$alkoxy, $CO_2R_{17}$ or $NR_{18}R_{19}$ groups, or 5- to 10-membered heteroaryl ring system containing 1, 2 or 3 heteroatoms selected from N, O or S optionaly substituted with one to three halogen, $NO_2$, CN, $C_1$–$C_6$alkyl, $C_1$–$C_6$haloalkyl, $C_1$–$C_4$alkoxy, $CO_2R_{17}$ or $NR_{18}R_{19}$ groups;

$R_3$ is phenyl optionally substituted with one to three halogen, $NO_2$, CN, hydroxy, $C_1$–$C_6$alkyl, $C_1$–$C_6$alkylthio, $C_1$–$C_6$haloalkyl, $C_1$–$C_6$alkoxy, phenyl, phenoxy, benzyl, benzyloxy, $SO_nR_{26}$, $SO_2NR_{21}R_{22}$, $CO_2R_{23}$ or $NR_{24}R_{25}$ groups, $C_5$–$C_7$cycloheteroalkyl optionally substituted with one or more halogen, $NO_2$, CN hydroxy, $C_1$–$C_6$alkyl, $C_1$–$C_6$alkylthio, $C_1$–$C_6$haloalkyl, $C_1$–$C_6$alkoxy, phenyl, phenoxy, benzyl, benzyloxy, $SO_nR_{26}$, $SO_2NR_{21}$, $R_{22}$, $CO_2R_{23}$ or $NR_{24}R_{25}$ groups, or 5- to 10-membered heteroaryl ring system containing 1, 2 or 3 heteroatoms selected from N, O or S optionally substituted with one or more halogen, $NO_2$, CN, hydroxy, $C_1$–$C_6$alkyl, $C_1$–$C_6$alkylthio, $C_1$–$C_6$haloalkyl, $C_1$–$C_6$alkoxy, phenyl, phenoxy, benzyl, benzyloxy, $SO_nR_{26}$, $SO_2NR_{21}R_{22}$, $CO_2R_{23}$ or $NR_{24}R_{25}$ groups;

$R_6$, $R_9$, $R_{12}$, $R_{17}$, $R_{20}$ and $R_{26}$ are each independently H or a $C_1$–$C_6$alkyl, $C_3$–$C_7$cycloalkyl, $C_1$–$C_6$haloalkyl, phenyl, $C_5$–$C_7$cycloheteroalkyl or 5- to 10-membered heteroaryl ring system containing 1, 2 or 3 heteroatoms selected from N, O or S group each optionally substituted;

n is 0 or an integer of 1 or 2; and $R_7, R_8, R_{10}, R_{11}, R_{13}, R_{14}, R_{18}, R_{19}, R_{21}, R_{22}, R_{24}$ and $R_{25}$ are each independently H or a $C_1$–$C_6$alkyl, $C_3$–$C_7$cycloalkyl, $C_1$–$C_6$haloalkyl, phenyl, $C_5$–$C_7$cycloheteroalkyl or 5- to 10-membered heteroaryl ring system containing 1, 2 or 3 heteroatoms selected from N, O or S group each optionally substituted or each of $R_7$ and $R_8$ or $R_{10}$ and $R_{11}$ or $R_{13}$ and $R_{14}$ or $R_{18}$ and $R_{19}$ or $R_{21}$, and $R_{22}$ or $R_{24}$ and $R_{25}$ may be taken together with the nitrogen atom to which they are attached to form a 5- to 7-membered ring optionally containing another heteroatom selected from O, N or S; or the pharmaceutically acceptable salts thereof.

2. The compound according to claim 1 wherein $R_2$ is an optionally substituted phenyl or 5- to 10-membered heteroaryl ring system containing 1, 2 or 3 heteroatoms selected from N, O or S group.

3. The compound according to claim 1 wherein $R_1$ is H, $C_1$–$C_3$alkyl or an optionally substituted benzyl group.

4. The compound according to claim 1 wherein $R_3$ is a $C_5$–$C_7$cycloheteroalkyl, 5- to 10-membered heteroaryl ring system containing 1, 2 or 3 heteroatoms selected from N, O or S group or phenyl group each optionally substituted with one or two halogen, CN, $NO_2$, $CF_3$, methoxy, carboxy or $SOR_{26}$ groups.

5. The compound according to claim 2 wherein $R_4$ is H or phenyl or $C_1$–$C_4$alkyl optionally substituted with one hydroxy or phenyl group.

6. The compound according to claim 2 wherein $R_3$ is a thienyl, pyridyl or phenyl group, each optionally substituted with one or two halogen, CN, $NO_2$, $CF_3$, methoxy, carboxy or $SOCH_3$ groups.

7. The compound according to claim 3 wherein $R_2$ is a phenyl group substituted with one or two halogen.

8. The compound according to claim 7 wherein $R_3$ is a phenyl group substituted with one $NO_2$ or $CF_3$ group.

9. The compound according to claim 8 wherein $R_1$ is H and $R_4$ is H or $CH_3$.

10. A pharmaceutical composition which comprises a pharmaceutically acceptable carrier and an effective amount of a compound of formula I

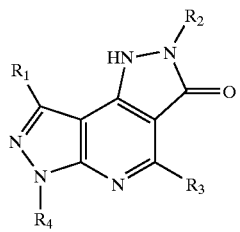

(I)

wherein
$R_1$ and $R_4$ are each independently H, $C_1$–$C_{10}$alkyl optionally substituted with one or more halogen, hydroxy, $C_1$–$C_4$alkoxy, $CO_2R_6$, $CONR_7R_8$, $C_3$–$C_7$cycloalkyl or optionally substituted phenyl groups, or phenyl optionally substituted with one to three halogen, hydroxy, $C_1$–$C_6$haloalkyl, $C_1$–$C_4$alkoxy, $CO_2R_9$, $NR_{10}R_{11}$ or CN groups;

$R_2$ is H, $C_1$–$C_6$alkyl optionally substituted with a phenyl, naphthyl or heteroaryl or 5- to 10-membered heteroaryl ring system containing 1, 2 or 3 heteroatoms selected from N, O or S group each group optionally substituted with one to three $C_1$–$C_6$alkyl, $C_1$–$C_6$haloalkyl, $C_1$–$C_4$alkoxy, hydroxy, CHO, $NO_2$, CN, $CO_2R_{12}$ or $NR_{13}R_{14}$ groups, phenyl optionally substituted with one to three halogen, $NO_2$, CN, hydroxy, $C_1$–$C_6$alkyl, $C_1$–$C_6$haloalkyl, $C_1$–$C_6$alkoxy, phenyl, phenoxy, benzyl, benzyloxy, $CO_2R_{17}$, $NR_{18}R_{19}$ or $CH_2CO_2R_{20}$ groups, naphthyl optionally substituted with one to three halogen, $NO_2$, CN, hydroxy, $C_1$–$C_6$alkyl, $C_1$–$C_6$haloalkyl, $C_1$–$C_6$alkoxy, phenyl, phenoxy, benzyl, benzyloxy, $CO_2R_{17}$, $NR_{18}R_{19}$ or $CH_2CO_2R_{20}$ groups, $C_5$–$C_7$cycloheteroalkyl optionally substituted with one to three halogen, $NO_2$, CN, $C_1$–$C_6$alkyl, $C_1$–$C_6$haloalkyl, $C_1$–$C_4$alkoxy, $CO_2R_{17}$ or $NR_{18}R_{19}$ groups, or 5- to 10-membered heteroaryl ring system containing 1, 2 or 3 heteroatoms selected from N, O or S optionally substituted with one to three halogen, $NO_2$, CN, $C_1$–$C_6$alkyl, $C_1$–$C_6$haloalkyl, $C_1$–$C_4$alkoxy, $CO_2R_{17}$ or $NR_{18}R_{19}$ groups;

$R_3$ is phenyl optionally substituted with one to three halogen, $NO_2$, CN, hydroxy, $C_1$–$C_6$alkyl, $C_1$–$C_6$alkylthio, $C_1$–$C_6$haloalkyl, $C_1$–$C_6$alkoxy, phenyl, phenoxy, benzyl, benzyloxy, $SO_nR_{26}$, $SO_2NR_{21}R_{22}$, $CO_2R_{23}$ or $NR_{24}R_{25}$ groups, $C_5$–$C_7$cycloheteroalkyl optionally substituted with one or more halogen, $NO_2$, CN hydroxy, $C_1$–$C_6$alkyl, $C_1$–$C_6$alkylthio, $C_1$–$C_6$haloalkyl, $C_1$–$C_6$alkoxy, phenyl, phenoxy, benzyl, benzyloxy, $SO_nR_{26}$, $SO_2NR_{21}$, $R_{22}$, $CO_2R_{23}$ or $NR_{24}R_{25}$ groups, or 5- to 10-membered heteroaryl ring system containing 1, 2 or 3 heteroatoms selected from N, O or S optionally substituted with one or more halogen, $NO_2$, CN, hydroxy, $C_1$–$C_6$alkyl, $C_1$–$C_6$alkylthio, $C_1$–$C_6$haloalkyl, $C_1$–$C_6$alkoxy, phenyl, phenoxy, benzyl, benzyloxy, $SO_nR_{26}$, $SO_2NR_{21}R_{22}$, $CO_2R_{23}$ or $NR_{24}R_{25}$ groups;

$R_6, R_9, R_{12}, R_{17}, R_{20}$ and $R_{26}$ are each independently H or a $C_1$–$C_6$alkyl, $C_3$–$C_7$cycloalkyl, $C_1$–$C_6$haloalkyl, phenyl, $C_5$–$C_7$cycloheteroalkyl or 5- to 10-membered heteroaryl ring system containing 1, 2 or 3 heteroatoms selected from N, O or S group each optionally substituted;

n is 0 or an integer of 1 or 2; and $R_7, R_8, R_{10}, R_{11}, R_{13}, R_{14}, R_{18}, R_{19}, R_{21}, R_{22}, R_{24}$ and $R_{25}$ are each independently H or a $C_1$–$C_6$alkyl, $C_3$–$C_7$cycloalkyl, $C_1$–$C_6$haloalkyl, phenyl, $C_5$–$C_7$cycloheteroalkyl or 5- to 10-membered heteroaryl ring system containing 1, 2 or 3 heteroatoms selected from N, O or S group each optionally substituted or each of $R_7$ and $R_8$ or $R_{10}$ and $R_{11}$ or $R_{13}$ and $R_{14}$ or $R_{18}$ and $R_{19}$ or $R_{21}$, and $R_{22}$ or $R_{24}$ and $R_{25}$ may be taken together with the nitrogen atom to which they are attached to form a 5- to 7-membered ring optionally containing another heteroatom selected from O, N or S; or the pharmaceutically acceptable salts thereof.

11. The composition according to claim 10 having a formula I compound wherein $R_2$ is an optionally substituted phenyl, thienyl or pyridyl group.

12. The composition according to claim 11 having a formula I compound wherein $R_1$ is H and $R_4$ is H or $CH_3$.

13. The composition according to claim 12 having a formula I compound wherein $R_3$ is a thienyl, pyridyl or phenyl group each optionally substituted with one or two halogen, CN, $NO_2$, $CF_3$, methoxy, carboxy or $SOCH_3$ groups.

14. The composition according to claim 13 having a formula I compound wherein $R_2$ is a phenyl group substituted with one or two halogen.

15. The composition according to claim 10 having a formula I compound selected from the group consisting of:

2-(3-fluorophenyl)-4-(3-nitrophenyl)-1,6-dihydrodipyrazolo[3,4-b:3',4'-d]pyridin-3(2H)-one;

2-(3-fluorophenyl-6-methyl-4-(3-nitrophenyl)-1,6-dihydrodipyrazolo[3,4-b:3',4'-d]-pyridin-3(2H)-one;

2-(4-chlorophenyl)-6-methyl-4-[3-(trifluoromethyl)phenyl]-1,6-dihydrodipyrazolo-[3,4-b:3',4'-d]pyridin-3(2H)-one;

2-(4-chlorophenyl)-6-methyl-4-(3-fluorophenyl)-1,6-dihydrodipyrazolo-[3,4-b:3'4'-d]pyridin-3(2H)-one;

4-(5-bromo-3-pyridinyl)-6-methyl-3-[(trifluoromethyl)phenyl]-1,6-dihydrodipyrazolo-[3,4-b:3',4'-d]pyridin-3(2H)-one;

4-(5-bromo-3-pyridinyl)-3-(4-fluorophenyl)-6-methyl-1,6-dihydrodipyrazolo-[3,4-b:3',4'-d]pyridin-3-(2H)-one;

methyl 3-{6-methyl-3-oxo-4-[3-(trifluoromethyl)phenyl]-3,6-dihydrodipyrazolo-[3,4-b:3',4'-d]pyridin-2(1H)-yl}benzoate;

2-chloro-5-{6-methyl-3-oxo-4-[3-(trifluoromethyl)phenyl]-3,6-dihydrodipyrazolo-[3,4-b:3',4'-d]pyridin-2(1H)-yl}benzoic acid;

4-(3-bromophenyl)-6-methyl-2-(4-nitrophenyl)-1,6-dihydrodipyrazolo[3,4-b:3',4'-d]-pyridin-3(2H)-one;

4-[4-(3-bromophenyl)-6-methyl-3-oxo-3,6-dihdrodipyrazolo[3,4-b:3',4'-d]pyridin-2(1H)-yl]-2-chlorobenzoic acid;

methyl 2-fluoro-4-{6-methyl-3-oxo-4-[3-(trifluoromethyl)phenyl]-3,6-dihydrodipyrazolo-[3,4-b:3',4'-d]pyridin-2-(1H)-yl}benzoate;

and the pharmaceutically acceptable salts thereof.

* * * * *